United States Patent [19]

Boeck et al.

[11] Patent Number: 5,082,819
[45] Date of Patent: Jan. 21, 1992

[54] CATALYST FOR CATALYTIC GAS PHASE OXIDATION OF OLEFINS INTO UNSATURATED ALDEHYDES AND METHOD FOR MAKING THE CATALYST

[75] Inventors: Wolfgang Boeck, Langenselbold; Dietrich Arntz, Oberursel, both of Fed. Rep. of Germany; Guenter Prescher, Larchmont, N.Y.; Werner Burkhardt, Brachtal, Fed. Rep. of Germany

[73] Assignee: Degussa Aktiengesellschaft, Frankfurt am Main, Fed. Rep. of Germany

[21] Appl. No.: 581,702

[22] Filed: Sep. 13, 1990

[30] Foreign Application Priority Data

Sep. 13, 1989 [DE] Fed. Rep. of Germany ....... 3930533

[51] Int. Cl.⁵ ............................................. B01J 27/192
[52] U.S. Cl. .................................................... 502/212
[58] Field of Search ......................................... 502/212

[56] References Cited

U.S. PATENT DOCUMENTS

| | | | |
|---|---|---|---|
| 2,941,007 | 6/1960 | Callahan et al. | 502/212 X |
| 3,639,269 | 2/1972 | Koberstein et al. | 502/212 |
| 4,245,118 | 1/1981 | Yamamoto et al. | 502/212 X |
| 4,438,217 | 3/1984 | Takata et al. | 502/205 |

FOREIGN PATENT DOCUMENTS

| | | |
|---|---|---|
| 0279374 | 8/1988 | European Pat. Off. . |
| 3125061 | 1/1981 | Fed. Rep. of Germany . |
| 3338380 | 4/1984 | Fed. Rep. of Germany . |
| 3740271 | 6/1989 | Fed. Rep. of Germany . |

Primary Examiner—W. J. Shine
Attorney, Agent, or Firm—Beveridge, DeGrandi & Weilacher

[57] ABSTRACT

A catalyst is described for the production of unsaturated aldehydes by means of oxidation with a oxygen-containing gas where an active mass, containing at least the elements Mo, Bi, P and O, as well as Si-containing carrier material, is used in the form of a catalyst body with a certain ratio between the outer surface and the volume and with a defined extent in terms of space, porosity, density, specific surface, breaking strength, abrasion, and gas through-flow capability. Also described is a method of making the catalyst.

21 Claims, 2 Drawing Sheets

CATALYST FOR CATALYTIC GAS PHASE OXIDATION OF OLEFINS INTO UNSATURATED ALDEHYDES AND METHOD FOR MAKING THE CATALYST

BACKGROUND OF THE INVENTION

The present invention relates to a catalyst for the heterogeneous catalyzed gas phase oxidation of propene into acrolein which is to be used in tube bundle reactors.

The strongly exothermal mixing of propene on heterogeneous catalyst with a oxygen-containing gas leads not only to the desired acrolein product but also to a series of undesirable by-products. It is known that by means of good dissipation of reaction heat, for example in tube bundle reactors, one can prevent the local overheating of the catalyst and the attendant increased formation of by-products.

It is furthermore known that by means of the size and outer shape of the catalyst body, one can influence the pressure loss of a catalyst charge. The internal structure of the catalyst body (porosity, length of diffusion paths) critically determines the mass transfer and heat transfer in the catalyst and thus, has a major bearing on selectivity along with the composition of the catalytically active mass.

High compression strength and abrasion resistance are basic pre-requisites if one is to be able to use a catalyst in industrial practice. High abrasion would lead to a situation where, during the filling of the tubes of a tube bundle reactor, the scattering of the pressure losses of the individual tubes would be high, which results in different flow through rates along with impairment of selectivity.

German Patent 31 25 061 describes a method for making acrolein, using shell catalysts. In the case of a shell catalyst, one can avoid the local overheating as a result of the temperature equalizing effect of the inert carrier; the diffusion paths for the gaseous reagents are relatively short in the thin shell.

German published patent application 33 38 380 describes ring-shaped or hollowed cylinder-shaped catalysts for the oxidation of propene into acrolein. These catalysts are made from a mass containing Mo, Fe, Bi and W. These catalysts can be considered as being derived from shell catalysts in that the inert core of the shell catalyst is replaced by an "inert cavity", while the shell is opened at two opposite points for access of the reagents to the cavity. Compared to the shell catalysts, these ring-like or hollowed cylinder-like catalysts reveal an enlarged ratio between the outer surface and the volume. As a result, the active mass is more accessible to the reagents. However, the low pressure loss and the high heat dissipation of the shell catalysts are present in these catalysts as well. To obtain sufficient mechanical strength in the case of the "hollowed catalyst", the active mass is highly compressed which results in the internal structure being adversely affected.

Ring-shaped catalysts, which have rounded end faces for the purpose of improving the filling capacity, are also described in European published patent application 0 184 790. Although neither the catalyst mass, nor a special production method are indicated; in particular no measures are illustrated for the attainment of a particularly favorable internal structure.

In order to make optimum use of active mass, the internal structure of the catalyst must be made so that a possible high reaction velocity will not be limited by an obstruction to mass transfer within the catalyst. European published patent application 0 279 374 shows an experiment aimed in this direction. A production method is described for a catalyst containing Mo, Fe and Bi, characterized by specific surface, pore volume, and pore distribution. Depending on the process used, however, one can obtain only catalyst particles of approximately spherical shape, that is to say, with a small ratio between surface and volume, or the particles would have to become very small. But, when it comes to industrial use, there are limits on that, due to the attendant high pressure loss.

Catalysts made and used according to the known state of the art present some disadvantages as regards the described aspects. By using differently shaped bodies, one either tries to shorten the diffusion paths, to avoid local overheating, or to attain an improved utilization of the catalyst volumes through a suitable internal structure of the catalysts. Individual measures of this kind so far have resulted in a situation where, with such catalysts used on an industrial scale, one can achieve only a comparatively unsatisfactory productivity per catalyst volume used during industrial production of acrolein. This is a matter of considerable disadvantage in economic terms because, to balance this out, one must use large and expensive reactors with a high filling volume for the catalyst to perform the reaction.

One of the objects of the present invention was to create a catalyst for making unsaturated aldehydes from olefins, particularly of acrolein from propene, through oxidation with a oxygen-containing gas. A catalyst is described which, with a large ratio between geometric surface and volume and simultaneously small low diffusion resistance, will overcome the disadvantages of the prior art and in particular will facilitate a surprisingly high productivity.

Another object of the invention was a manufacturing process for the described catalyst in terms of its basic composition and the further developed variants.

DETAILED DESCRIPTION OF THE INVENTION

The catalyst according to the present invention is characterized by the following properties:

(a) an active mass containing at least the elements molybdenum, bismuth, phosphorus, and oxygen in atomic ratios of:

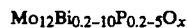

$$Mo_{12}Bi_{0.2-10}P_{0.2-5}O_x$$

as well as silicon-containing carrier material;

(b) having any desirable geometrical shape whose ratio between the outer surface $O_p$ and the volume $V_p$ is above 1.6 $mm^{-1}$ and in which the spatial dimension, described by the diameter of a sphere that just barely encloses it, is less than 7.5 mm;

(c) a porosity of the catalyst body amounting to at least 0.46, the absence of micropores (<2 nm), a mesopore volume (2–30 nm) amounting to at least 0.03 $cm^3/g$, preferably 0.03–0.10 $cm^3/g$, as well as a macropore volume (>30 nm) amounting to at least 0.30 $cm^3/g$, preferably 0.30–0.50 $cm^3/g$;

(d) a mercury density of the catalyst body amounting to at least 1.25 g/cm$^3$, preferably 1.25–1.85 g/cm$^3$;
(e) a specific BET surface area amounting to at least 10 m$^2$/g, preferably 10–25 m$^2$/g;
(f) a breaking strength of at least 6.0 N;
(g) an abrasion of less than 50 mg/g catalyst;
(h) a pressure loss of less than 1,600 Pa/m of a catalyst charge inserted into a tube with a diameter of 2 cm.

The catalyst according to the present invention, in all of the mixing oxide formulations that are relevant to gas phase oxidation and which contains at least molybdenum, bismuth, and phosphorus in the atomic ratios described, offers great advantages in regards to the obtainable space-time yield. The activity required for a high space-time yield is facilitated by the favorable ratio between the outer surface and volume and the favorable internal structure. As a result of the increased ratio between the surface and the volume, the particular catalytically active mass is readily accessible for the reagents, and the diffusion paths are short. The result of the favorable internal structure is that the diffusion resistance in the interior of the catalyst is low.

The high activity, caused by the large internal surface, can thus be well utilized. Basically, the reduced diffusion resistance in the catalyst body also favorably influences the selectivity.

Figure 1A:
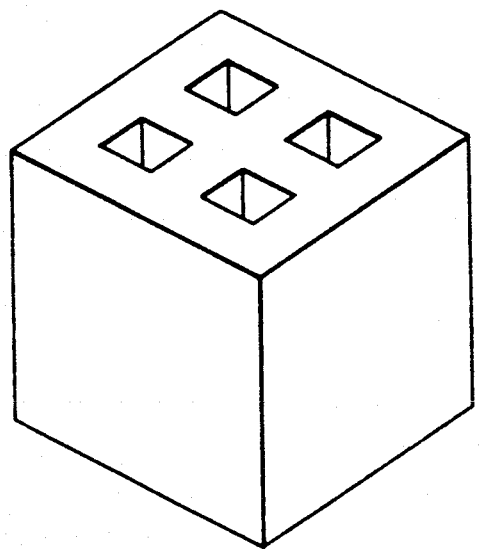
FIGS. 1a, 1b, 1c, 2a, 2b, and 2c show examples of various shapes of the body of the catalyst.
Figure 1B:
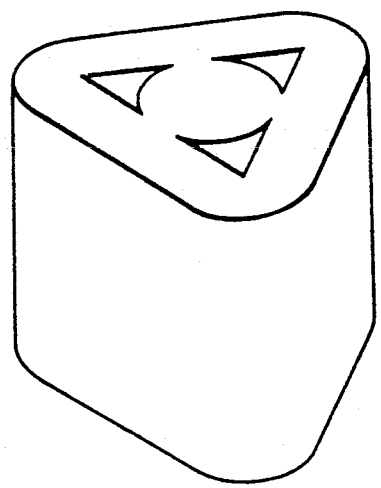
Figure 1C:
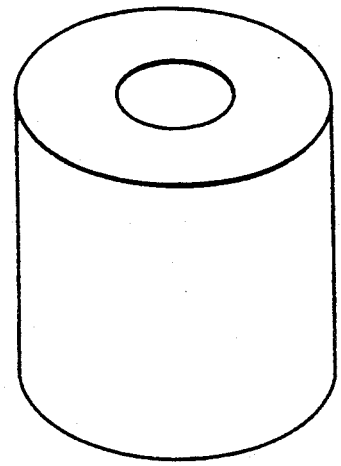
Figure 2A:
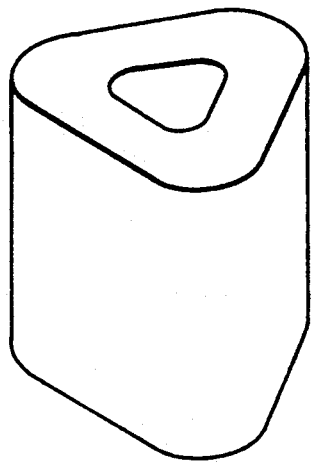
Figure 2B:
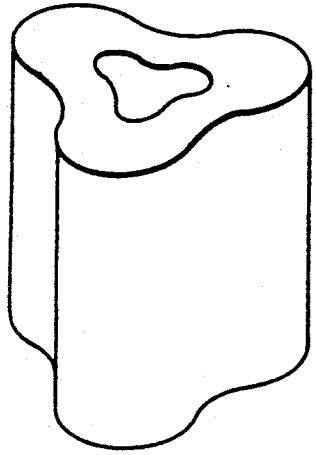
Figure 2C:
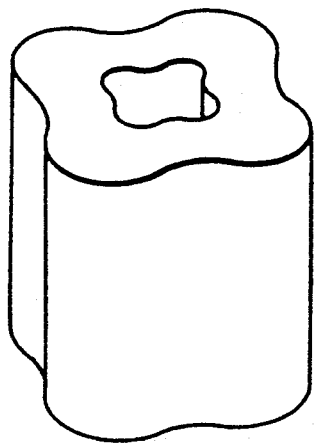

The body of the catalyst according to the invention can have any desired geometrical shapes. FIGS. 1–2 show examples of various body shapes.

Among the catalyst formulations developed with the previously mentioned basic components, a mass containing the following composition proved to be particularly suitable:

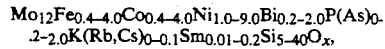
$Mo_{12}Fe_{0.4-4.0}Co_{0.4-4.0}Ni_{1.0-9.0}Bi_{0.2-2.0}P(As)_{0.2-2.0}K(Rb,Cs)_{0-0.1}Sm_{0.01-0.2}Si_{5-40}O_x$, whereby the element silicon is present as a pyrogenic or highly-dispersed precipitated silicic acid, silicic acid brine, fine-particle aluminum silicate, preferably in the form of montmorillonite.

A preferred variant of this formulation comprises a mass containing the following composition:

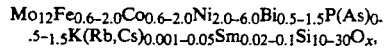
$Mo_{12}Fe_{0.6-2.0}Co_{0.6-2.0}Ni_{2.0-6.0}Bi_{0.5-1.5}P(As)_{0.5-1.5}K(Rb,Cs)_{0.001-0.05}Sm_{0.02-0.1}Si_{10-30}O_x$, whereby the element silicon is present in the form of pyrogenic SiO$_2$ and montmorillonite in a weight ratio of 1:0.5 to 1:4.

It is preferable to make sure that the montmorillonite will have specific surface according to BET of less than 2.0 m$^2$/g, reduced, in other words, by means of a calcination treatment.

The manufacturing process for the described catalyst comprises the following steps:
(a) mixing a suspension of the coprecipitate, obtained in the known manner, by combining salt solutions of the catalytically active elements (except for Si) with the insoluble, silicon-containing solid, and spray-drying the suspension thus obtained under conditions that provide an initial temperature of the drying air amounting to 300° C.–600° C. and a temperature, during the separation of the dried powder, amounting to 120° C.–220° C., as well as an atomization intensity that generates a spray dried powder with an average particle diameter of less than 30 μm, whereby the duration of time spent by the spray dried powder in the dryer amounts to 2–25 seconds;
(b) calcining the dried spray dried powder in a kiln, preferably a rotary cylindrical kiln, with duration of between 5 and 60 minutes and a peak temperature of the spray dried powder of 320° C. to 480° C.;
(c) extruding the calcined sprayed dried powder with 5 to 40 weight %, related to the quantity of the spray dried powder, of a pore forming agent (which is completely decomposable at a temperature of less than 400° C.) and with a quantity of wetting agent, lubricant, and binding agent (which totals no more than 40 weight % of the sprayed dried powder quantity) that yield an extrudable mass at a temperature of less than 80° C., in the desired geometrical shape, at a pressure of less than 50 bar, and subdividing the extruded strand by cutting it to the length of the desired body;
(d) drying the individual bodies in a kiln, preferably a rotary cylindrical kiln, to carefully burn out the decomposable substance present and then tempering in the air current with a duration of 5 to 60 minutes and a peak temperature of 450° C. to 650° C. measured in the charge of the individual bodies.

The process is based on a procedure which comprises the combination of a spray drying of the initial material at defined conditions, intermediate tempering within a specified temperature span, and extrusion of the calcined spray dried powder with defined quantities of a pore forming agent and customary processing aids in a quantity limited in terms of weight under accurate extrusion conditions and with final tempering in air at a raised temperature level. According to one preferable version of the method according to the present invention, the pore forming agent used here is solid pentaerythritol with an average particle diameter of less than 40 μm. In addition to pentaerythritol, one could also use cellulose powder, urea, oxalic acid, and polyvinyl alcohol as pore forming agents.

As a result of the spray drying of the suspension of the coprecipitate, one obtains a spherical spray dried powder with high internal porosity under the conditions specified. As a result, one can produce the internal surface which is large for such catalysts. As a result of intermediate tempering, all decomposable constituents are removed from the primary particle so that there cannot be any reduction of the strength during final tempering.

As a result of the pore forming agent, which is added during the extrusion process, preferably in the particle size range of the primary particle, a macropore system is formed during final tempering as a result of which the highly-active mesoporous primary particles become easily accessible to the reagents. During extrusion, one can advantageously use as lubricant petroleum or water and as wetting agent and binding agent or lubricant a 1–10% aqueous methylcellulose solution, preferably in the form of an oil-in-water emulsion or one can use methylcellulose powder as a dry binder.

Final tempering at 450° C.–650° C. includes a prior careful burn-out process during the heating phase. The burn-out and tempering of the extruded individual bodies, however, can also be performed in separate steps. In both cases one gets particularly good results if one conducts the extruded individual bodies and the air current during the burn-out process in a direct flow current and if one performs the burn-out at a maximum of 400° C.

When one uses the new catalyst for the oxidation of olefins into unsaturated aldehydes by means of a oxygen-containing gas, for example in the case of the presently preferred illustration of acrolein from propene, one can employ very favorable operating conditions which lead to higher productivity. The reaction is performed at a temperature of 300° C.–380° C. and a pressure of 1.4–2.2 bar. Here, the reactants propene, air, inert gas, and water are supplied to the catalyst charged in a ratio of 1:6–9:3–12:0–5 at a specific charge of 2–8 mol propene/dm³ catalyst charged/hr. In place of inert gas one preferably uses the waste gas from the reaction, from which the condensable constituents had been separated. Particularly good results are obtained when one uses a tube bundle reactor whose tubes have an inside diameter of 16–25 mm.

The invention will be explained below with the help of practical examples:

EXAMPLES

The variables referred to in the examples are determined as follows:

(1) Determination of Porosity

Porosity is calculated from the mercury and helium density in accordance with the following equation: Porosity=(1-Hg density/He density). 100 "Porosity" is defined as the percentage share of the empty volume of the catalyst mass out of the total volume of that mass. It is dimensionless.

(2) Determination of the Mesopore Volume

Barrett, E. P.; Joyner, L. G.; Halenda, P. P., *J. Am. Chem. Soc.* (1951), volume 73, page 373;

(3) Determination of the Macropore Volume

Hg injection process with Carlo-Erba porosimeter, 200 to 1,000 bar pressure;

(4) Determination of Bulk Density, Mercury Density (Apparent Density) and Helium Density (Real Density)

The bulk density is determined by uniformly filling a straight steel tube, with an inside diameter of 20 mm, with 200 g catalyst within one minute, and measuring the height of the resultant catalyst charge.

The mercury density is determined by filling 2 mg of the catalyst, which has been comminuted down to 200 μm, into a pycnometer with a volume of 25 ml and carefully filling the pycnometer with mercury. From the masses of the mercury, which are needed to fill the pycnometer with or without catalyst sample, and from the mass of the catalyst sample itself, one gets the mercury density (or apparent density) of the catalyst. The helium density (or real density) of the catalyst mass is determined with a Beckmann air comparison pycnometer.

(5) Determination of BET Surface According to DIN (German Industrial Standard) 66131 (Measurement Gas $N_2$)

Heating conditions: dried for 15 hours at 100° C., degassed in vacuo for 1 hour at 200° C.

(6) Determination of Breaking Strength

Measured perpendicularly to the direction of extrusion with an Erweka TBA 28, arithmetic mean from 100 individual measurements ± standard deviation;

(7) Determination of Abrasion

Measured with Roche TA3-R Friabilator, initial weighing 50 g, 10 rpm, duration of loading 5 minutes; result indicated as abrasion of catalyst particles <1 mm in mg/g catalyst;

(8) Determination of Pressure Loss

Catalyst is uniformly introduced for 1 minute into a tube having an internal diameter of 2 cm, which is closed at its lower end by a wire gauze, in such a quantity that the height of the catalyst bed is 1 m. Air at 20° C. is then passed through the catalyst bed at a rate of 1 Nm³/h and the pressure loss is measured;

(9) Determination of Particle Size Distribution

This is done with a CILAS 715 Granulometer. As the suspension liquid, one adds ethanol. To destroy the agglomerates, one deagglomerate for one minute with ultrasound.

(10) Determination of Catalytic Properties

The catalystic effect of the ready catalyst is tested in a technical (industrial) tube reactor with an inside diameter of 20.5 mm, which is cooled from the outside by means of a salt bath, at a catalyst charge length of 250 cm, on the basis of the conversion of propene into acrolein. The reaction is performed at a feeding of 5.8 mol propene/hr (or 5.2 mol propene/hr, characterized by an asterisk in Table 3), 43.5 mol air/hr, 34.8 mol waste gas (composition: 5% $O_2$, 1% propene, 94% inert gas ($CO_2$, CO, $N_2$, Ar, propane)) and 2.9 mol $H_2O$/hr and a pressure of 1.8 bar at the entrance into the catalyst charge. The adjusted salt bath temperature, the maximum obtained excess temperature (exothermal) in the middle of the tube and the measured conversion and yields are compiled in Table 3.

The acrolein yield (%) is defined as:

$$\frac{\text{mol/hr acrolein formed}}{\text{mol/hr propene supplied}} \cdot 100$$

The acrylic acid yield (%) is defined as:

$$\frac{\text{mol/hr acrylic acid formed}}{\text{mol/hr propene supplied}} \cdot 100$$

The conversion of propene % is defined as:

$$1 - \frac{\text{mol/hr of propene coming out of the reaction pipe}}{\text{mol/hr propene supplied into the reaction pipe}} \cdot 100$$

Acrolein selectivity (%) is defined as:

$$\frac{\text{acrolein yield}}{\text{propene conversion}} \cdot 100$$

Acrylic acid selectivity (%) is defined as:

$$\frac{\text{acrylic acid yield}}{\text{propene conversion}} \cdot 100$$

Acrolein productivity is defined as:

g/hr acrolein formed
catalyst charged

The following examples relate to the manufacturing and use of the catalysts listed in Table 1.

The catalyst composition given in Table 1 under Example 1, which is already described in German Patent 1,129,150, was produced in the geometrical shape III in FIG. 1.

EXAMPLE 1

The coprecipitate for making the active catalyst phase is produced by introducing, at room temperature and while stirring forcefully, 4918 g $Bi(NO_3)_3.5H_2O$, 2299 g $H_2MoO_4$ and 134 g 85% $H_3PO_4$ into 3380 g of water which has been mixed beforehand with 460 g concentrated $HNO_3$. The resultant suspension is put into 6338 g aqueous 30% silica brine suspension. The suspension is diluted with 4250 g of water and is dried in a spray drier at a drying air entry temperature of 500° C. The ratio between the drying air volume and the sprayed suspension quantity is adjusted so that one gets a duration of 6 seconds spent by the spray dried powder in the spray dryer. The atomization intensity is selected so that one gets a spray dried powder with an average spray diameter of $dp=6$ μm.

The spray dried powder is calcined for 60 minutes in a rotary cylindrical kiln at a maximum temperature, in the spray dried powder, of 350° C.

1.5 kg of the calcined powders are lined up in a kneader/extruder combination and are mixed with 0.375 kg of pentaerythritol, having an average particle diameter of $dp=40$ μm ("very finely ground"), for a period of 5 minutes. To this mixture one adds 600 g of a 10% tylose solution in which 100 g petroleum had been emulsified beforehand. This mass is now kneaded until a homogeneous plastic state has been attained. Extrusion then takes place at a pressure of 10 bar at a temperature of 20° C. in the extruded mass. The extruded hollowed strand is cut off after every 5 mm, the cut rings (with a diameter of 5 mm, a length of 5 mm and an inside diameter of 1.8 mm) are dried at room temperature.

The dried rings are put into a heated rotary pipe and are heated at an rpm of 2 min$^{-1}$ and an air surplus to a peak temperature of 550° C. in the charge that migrates through the rotary pipe. The time spent in the rotary pipe is 60 minutes.

The physical properties measured in the catalyst composition, or its preliminary stages, are compiled in Table 2. The catalyst effect during the production of acrolein is shown in Table 3.

In the following Comparison Example 1 there is a description of how the catalyst make-up described in German Patent No. 1,129,150 is shaped in the usual manner to form tablets with dimensions of 5×5 mm.

COMPARATIVE EXAMPLE 1

The coprecipitate for making the active catalyst phase is made as in Example 1. The suspension obtained is evaporated into dryness in the rotation evaporator in a vacuum. The dried residue is comminuted and is screened through a 1 mm screen. 5 weight % stearic acid is mixed as a compression aid with the obtained powder. The mixture is shaped into tablets, with dimensions of 5×5 mm, in a tablet-making machine. The tablets are tempered in a circulating air drying cabinet, with additional fresh air supplied, for 16 hours at 538° C.

The catalyst composition, given in Table 1 under Example No. 2, was made as follows in the geometrical shape III in FIG. 1:

EXAMPLE 2

The coprecipitate for making the active catalyst phase is produced by dissolving 484.8 g $Fe(NO_3)_3.9H_2O$, 291.0 g $Co(NO_3)_2.6H_2O$, 1163.2 g $Ni(NO_3)_2.6H_2O$ and 2.5 g $KNO_3$ in 3.1 liters of water; and, while stirring, at 90° C., one first of all adds a solution of 17.4 g $Sm_2O_3$ in 106 g of concentrated $HNO_3$. While stirring further, one adds to this solution 601 g highly-dispersed silicic acid (Aerosil 200) and 1202 g of tempered montmorillonite (specific surface according to BET <1 $m^2/g$). In a separate vessel, at 60° C., one prepares a solution of 2118.6 g $(NH_4)_6Mo_7O_{24}.6H_2O$ in 2.7 liters $H_2O$; and to it we add 92.2 g of 85% $H_3PO_4$ while stirring intensively.

After that, the two solutions are combined amid intensive stirring and one adds a solution of 242.5 g $Bi(NO_3)_3.5H_2O$ in 204 g of 8.2% $HNO_3$. The suspension thus obtained is dried in a sprayed drier at a drying air entry temperature of 550° C. The ratio between drying air volume and sprayed suspension quantity is adjusted here so that one gets an exit temperature of 170° C. and the suspension quantity is adjusted so that one gets the duration of 6 seconds spent by the spray dried powder in the spray drier. The atomization intensity is selected so that one gets a spray dried powder with an average diameter of $dp=25$ μm. The spray dried powder is calcined for 30 minutes in a rotary cylindrical kiln at a maximum temperature of the spray dried powder of 420° C.

1.6 kg of the calcined spray dried powder is arranged in a kneader/extruder combination and is mixed with 0.4 kg pentaerythritol, having an average particle diameter of $dp=40$ μm ("very finely ground"), for a period of 5 minutes. To this mixture one adds 493 g of a 6 weight % tylose solution in which 26.6 g petroleum had first been emulsified. This mass is now kneaded until a homogeneous plastic state has been attained. Extrusion then takes place at a pressure of 10 bar and a temperature of 30° C. in the extruded mass. The extruded hollow strand is cut off after every 5 mm, the rings that are cut off (having a diameter of 5 mm, a length of 5 mm and an inside diameter of 1.8 mm) are carefully dried at 80° C.

The dried rings are placed in a heated rotary tube and are heated at an rpm of 2 min.$^{-1}$ and air surplus to a peak temperature of 600° C. in the charge migrating through the rotary tube. The time spent in the rotary tube here is 30 minutes.

The physical properties, measured in the catalyst composition or its preliminary stages, are compiled in Table 2, and the catalyst effect during the production of acrolein is shown in Table 3.

In Example 3, the same catalyst composition was made as in Example 2, with the geometrical shape VI in FIG. 2.

EXAMPLE 3

In accordance with Example 2, the coprecipitate of the active catalyst phase is made, dried, calcined, and kneaded in a kneader/extruder combination until a homogeneous plastic state is obtained. Extrusion takes place at a pressure of 15 bar and a temperature of 32° C.

in the extruded mass. The hollowed strand, extruded in shape VI in FIG. 2, is cut off after every 5 mm, the catalyst blanks which have been cut off are dried and are tempered in the rotary tube as in Example 2.

In Example 4, the same catalyst composition was made as in Example 2 with the geometrical shape II in FIG. 1.

EXAMPLE 4

In accordance with Example 2, the coprecipitate of the active catalyst phase is made, dried, calcined, and kneaded in a kneader/extruder combination until a homogeneous plastic state has been attained. Extrusion takes place at a pressure of 15 bar and a temperature of 32° C. in the extruded mass. The hollow strand extruded in shape II of FIG. 1 is cut off after every 5 mm, the catalyst blanks which have been cut off are dried and are tempered in the rotary tube as shown in Example 2. In Comparison Example 2, the same catalyst composition was extruded as in Example 2 in the shape of strand blanks.

COMPARISON EXAMPLE 2

In accordance with Example 2, the coprecipitate of the active catalyst phase is made, dried, calcined, and kneaded in a kneader/extruder combination until a homogeneous plastic state has been attained. Extrusion takes place at a pressure of 8 bar and a temperature of 25° C. in the extruded mass. The catalyst mass extruded, in the shape of a full strand with a diameter of 5 mm, is cut off after every 5 mm; the catalyst blanks which have been cut off are dried and are then tempered in the rotary pipe as shown in Example 2.

In the following Examples 5, 6 and 7, the various catalyst compositions are made in geometrical shape III in FIG. 1 as in Example 2.

EXAMPLE 5

The coprecipitate for making the active catalyst phase is obtained by dissolving 242.4 g $Fe(NO_3)_3.9H_2O$, 232.8 g $Co(NO_3)_2.6H_2O$, 1744.8 g $Ni(NO_3)_2.6H_2O$ and 5.1 g $KNO_3$ in 3.1 liters of water; and while stirring, at 90° C., one first of all adds a solution of 34.9 g $Sm_2O_3$ in 212 g of concentration $HNO_3$. To this solution one adds, while stirring, 300.5 g of highly dispersed silicic acid (Aerosil 200) and 300.5 g tempered montmorillonite (specific surfaces according to BET $<1$ m$^2$/g). In a separate vessel, at 60° C., one prepares a solution of 2118.6 g $(NH_4)_6Mo_7O_{24}.6H_2O$ in 2.7 liters $H_2O$ and to it, while stirring intensively, one adds 115.3 g of 85% $H_3PO_4$. Thereafter, both solutions are combined amid intensive stirring and a solution of 485.1 g $Bi(NO_3)_3.5H_2O$ in 408 g 8.2% $HNO_3$ is added. The suspension thus obtained is dried in a spray drier at a drying air entry temperature of 550° C. The ratio between drying air volume and sprayed suspension quantity is adjusted here so that one gets an exit temperature of 170° C. and the suspension quantity is adjusted so that one gets a time of 6 seconds spent by the sprayed dried powder in the spray drier. The atomization intensity is selected so that one gets a sprayed particle with an average diameter dp=25 μm. The dried spray dried powder is calcined for 30 minutes in a rotary cylindrical kiln at a maximum temperature of the spray dried powder of 420° C.

The further processing of the calcined spray dried powder takes place as in Example 2, except that the extruded hollowed strand has an inside diameter of 2 mm.

EXAMPLE 6

The coprecipitate for making the active catalyst phase is obtained by dissolving 808.0 g $Fe(NO_3)_3.9H_2O$, 320.1 g $Co(NO_3)_2.6H_2O$, 1744.8 g $Ni(NO_3)_2.6H_2O$ and 0.1 g $KNO_3$ in 3.1 liters of water; and, while stirring, at 90° C., one first of all adds a solution of 34.9 g $Sm_2O_3$ in 212 g of concentrated $HNO_3$. To this solution, while stirring further, one adds 600.9 g of high dispersed silicic acid (Aerosil 200) and 1201.8 g of tempered montmorillonite (specific surfaces according to BET $<1$ m$^2$/g). In a separate vessel, at 60° C., one prepares a solution of 2118.6 g $(NH_4)_6Mo_7O_{24}.6H_2O$ in 2.7 liters $H_2O$ and to it, while stirring intensively, one adds 115.3 g of 85% $H_3PO_4$. Thereafter, both solutions are combined while stirring intensively and one adds a solution of 485.1 g $Bi(NO_3)_3.5H_2O$ in 408 g 8.2% $HNO_3$. The suspension thus obtained is dried in a spray drier at a drying air entry temperature of 550° C. The ratio between drying air volume and spray suspension quantity is adjusted here so that one gets an exit temperature of 170° C. and the suspension quantity is adjusted so that the spray dried powder will spend 6 seconds in the spray drier. The atomization intensity is selected so that one gets a spray dried powder with an average diameter of small dp=25 μm. The spray dried powder is calcined in a rotary cylindrical kiln for a period of 30 minutes and at a maximum temperature, in the spray dried powder, of 420° C.

The further processing of the calcined sprayed dried powder takes place as in Example 5.

EXAMPLE 7

The coprecipitate for making the active catalyst phase is obtained by dissolving 646.4 g $Fe(NO_3)_3.9H_2O$, 174.6 g $Co(NO_3)_2.6H_2O$, 1744.8 g $Ni(NO_3)_2.6H_2O$ and 0.1 g $KNO_3$ in 3.1 liters of water; and, while stirring, at 90° C., one first of all adds a solution of 34.9 g $Sm_2O_3$ in 212 g of concentrated $HNO_3$. To this solution while stirring further, one adds 600.9 g highly dispersed silicic acid (Aerosil 200) and 1201.8 g of tempered montmorillonite (specific surface according to BET $<1$ m$^2$/g). In a separate vessel, at 60° C., one prepares a solution of 2118.6 g $(NH_4)_6Mo_7O_{24}.6H_2O$ in 2.7 liters $H_2O$ and, while stirring intensively, one adds to it 115.3 g of 85% $H_3PO_4$. Thereafter, both solutions are combined while stirring intensively and a solution of 727.7 g $Bi(NO_3)_3.5H_2O$ in 612.0 g of 8.2% $HNO_3$ is added. The suspension thus obtained is dried in a spray drier at a drying air entry of 550° C. The ratio between drying air volume and spray suspension quantity is adjusted here so that one obtains an exit temperature of 170° C. and the suspension quantity is adjusted so that one obtains a duration of 6 seconds spent by the spray dried powder in the spray dryer. The atomization intensity is selected so that one gets a spray dried powder with an average diameter of dp=25 μm. The spray dried powder is calcined for 30 minutes in a rotary cylindrical kiln at a maximum temperature of the spray dried powder of 420° C.

The further processing of the calcined spray dried powder takes place as in Example 5.

In Example 8, the same catalyst composition as in Example 2 is shaped, except that, in Example 8, one used cellulose powder instead of pentaerythritol, as pore forming agent.

EXAMPLE 8

The calcined spray dried powder is made as in Example 2.

1.6 kg of the calcined spray dried powder are arranged in a kneader/extruder combination and are mixed with 0.4 kg of cellulose powder, with an average particle diameter of dp=36 μm, as pore forming agent for a period of 5 minutes.

The further processing takes place as in Example 2.

In Comparison Example 3, the catalyst is made as in Example 2 but no pore forming agent is added during shaping.

attained. Extrusion takes place in shape III of FIG. 1 at a pressure of 14 bar and a temperature of 32° C. in the extruded mass.

The further processing of the extruded mass takes place as in Example 2, whereby the peak temperature during tempering in the rotary tube is raised to 620° C.

It will be appreciated that the instant specification and claims are set forth by way of illustration and not limitation and that various modifications and changes may be made without departing from the spirit and scope of the present invention.

German Patent Application P 39 30 533.3 is incorporated by reference.

TABLE 1

CATALYST COMPOSITION (ATOMIC NUMBERS)

| EXAMPLE | COMPARISON EXAMPLE | Mo | Fe | Co | Ni | Bi | P | K | Sm | Si (as montmorillonite + highly dispersed silicic acid) |
|---|---|---|---|---|---|---|---|---|---|---|
| 1 | 1 | 12 | — | — | — | 10.1 | 1.2 | — | — | 30 |
| 2, 3, 4, 8 | 2, 3 | 12 | 1.2 | 1.0 | 4.0 | 0.5 | 0.8 | 0.025 | 0.1 | 30 |
| 5 | | 12 | 0.6 | 0.8 | 6.0 | 1.0 | 1.0 | 0.05 | 0.2 | 10 |
| 6 | | 12 | 2.0 | 1.1 | 6.0 | 1.0 | 1.0 | 0.001 | 0.2 | 30 |
| 7 | | 12 | 1.6 | 0.6 | 6.0 | 1.5 | 1.0 | 0.001 | 0.2 | 30 |

1 Example
2 Comparison Example
3 (as montmorillonite + highly dispersed silicic acid)

TABLE 2

PHYSICAL-CHEMICAL CATALYST CHARACTERIZATION

| Ex. | Comp. Ex. | Op/Vp mm$^{-1}$ | dK* mm | porosity | Vmeso ml/g | Vmacro ml/g | charge g/ml | He- g/ml | Hg-density g/ml | BET-Surface m$^2$/g | fracture resistance N | abrasion mg/g | p Pa/m |
|---|---|---|---|---|---|---|---|---|---|---|---|---|---|
| 1 | | 1.65 | 7.1 | 0.60 | 0.04 | 0.46 | 0.71 | 3.97 | 1.58 | 13 | 6.8 | 42 | 1440 |
| | 1 | 1.2 | 7.1 | 0.34 | 0.10 | 0.17 | 1.09 | 4.04 | 2.60 | 19 | 26.9 | 56 | 1620 |
| 2 | | 1.65 | 7.1 | 0.51 | 0.05 | 0.38 | 0.76 | 3.48 | 1.71 | 14 | 14.9 | 16 | 1450 |
| 3 | | 2.00 | 7.1 | 0.62 | 0.05 | 0.48 | 0.60 | 3.49 | 1.30 | 16 | 9.8 | 32 | 1400 |
| 4 | | 2.10 | 7.1 | 0.62 | 0.04 | 0.42 | 0.70 | 2.54 | 1.30 | 16 | 15.4 | 48 | 1340 |
| | 2 | 1.2 | 7.1 | 0.64 | 0.04 | 0.42 | 0.79 | 3.59 | 1.30 | 16 | 18.9 | 20 | 1520 |
| 5 | | 1.73 | 7.1 | 0.56 | 0.03 | 0.39 | 0.70 | 4.02 | 1.77 | 12 | 6.2 | 8 | 1260 |
| 6 | | 1.73 | 7.1 | 0.56 | 0.04 | 0.30 | 0.72 | 4.05 | 1.79 | 11 | 10.7 | 4 | 1190 |
| 7 | | 1.73 | 7.1 | 0.56 | 0.03 | 0.29 | 0.73 | 4.08 | 1.81 | 12 | 7.7 | 14 | 1290 |
| 8 | | 1.65 | 7.1 | 0.62 | 0.04 | 0.33 | 0.76 | 3.51 | 1.30 | 16 | 14.4 | 18 | 1430 |
| | 3 | 1.65 | 7.1 | 0.44 | 0.05 | 0.25 | 0.87 | 3.46 | 1.93 | 13 | 16.8 | 11 | 1400 |

*dK = diameter of sphere just barely enclosing catalyst

TABLE 3

CATALYST EFFECT DURING PRODUCTION OF ACROLEIN

| Example | Comparison Example | Salt bath temp. | Conversion % | Exothermal degree % | Acrolein yield % | Acrylic acid yield % | Acrolein selectivity % | Acrylic acid selectivity % | Productivity g/Acrol./dm$^3$ catal./hr |
|---|---|---|---|---|---|---|---|---|---|
| 1 | | 431 | 84.0 | 36 | 56.1 | 5.7 | 66.8 | 6.8 | 221 |
| | 1 | 422 | 82.5 | 38 | 50.9 | 5.2 | 61.7 | 6.3 | 180* |
| 2 | | 331 | 94.2 | 81 | 81.8 | 7.0 | 86.8 | 7.4 | 322 |
| 3 | | 347 | 93.4 | 78 | 81.4 | 7.3 | 87.1 | 7.8 | 320 |
| 4 | | 345 | 92.7 | 76 | 80.9 | 7.1 | 87.2 | 7.7 | 318 |
| | 2 | 330 | 93.1 | 78 | 77.6 | 8.5 | 83.3 | 9.1 | 273* |
| 5 | | 364 | 91.1 | 72 | 80.3 | 8.7 | 88.1 | 9.5 | 316 |
| 6 | | 344 | 90.9 | 76 | 80.1 | 9.0 | 88.1 | 9.9 | 315 |
| 7 | | 359 | 91.3 | 72 | 80.3 | 8.8 | 87.9 | 9.6 | 316 |
| 8 | | 348 | 92.6 | 77 | 80.4 | 6.9 | 86.8 | 7.5 | 317 |
| | 3 | 350 | 90.0 | 74 | 77.1 | 6.0 | 85.6 | 6.7 | 272* |

*feeding in 5.2 mol propene/hr

COMPARISON EXAMPLE 3

The calcined spray dried powder is made as in Example 2. 1.6 kg of the calcined spray dried powder is placed in a kneader/extruder combination. To it one adds 394.4 of a 6 weight % tylose solution in which 21.3 g of petroleum have been emulsified beforehand. This mass is kneaded until a homogeneous plastic state is

What is claimed is:

1. A catalyst for the production of unsaturated aldehydes from olefins, especially of acrolein from propene, through oxidation with a oxygen-containing gas, said catalyst comprising the following properties:

(a) an active mass comprising at least the elements molybdenum, bismuth, phosphorus, and oxygen in atomic ratios of:

$$Mo_{12}Bi_{0.2-10}P_{0.2-5}O_x$$

as well as silicon-containing carrier material wherein X denotes the number of oxygen atoms which satisfies the valences of the other elements;

(b) a catalyst body having any desired geometrical shape whose ratio between the outside surface Op and the volume Vp is above 1.6 mm$^{-1}$ and in which the spatial dimension, described by the diameter of a sphere which barely encloses it, is smaller than 7.5 mm;

(c) a porosity of the catalyst amounting to at least 0.46, the absence of micropores (<2 nm), a mesopore volume (2-30 nm) of at least 0.03 cm$^3$/g as well as a macropore volume (>30 nm) of at least 0.30 cm$^3$/g;

(d) a mercury density of the catalyst body amounting to at least 1.25 g/cm$^3$;

(e) a specific BET surface area amounting to at least 10 m$^2$/g;

(f) a breaking strength of at least 6.0N;

(g) an abrasion of less than 50 mg/g catalyst; and (h) a pressure loss of less than 1600 Pa/m of a catalyst charge inserted into a tube with a diameter of 2 cm.

2. A catalyst according to claim 1, wherein said mesopore volume is 0.03-0.10 cm$^3$/g.

3. A catalyst according to claim 1, wherein said macropore volume is 0.30-0.50 cm$^3$/g.

4. A catalyst according to claim 1, wherein said mercury density is 1.25-1.85 g/cm$^3$.

5. A catalyst according to claim 1, wherein said specific BET surface area is 10-25 m$^2$/g.

6. A catalyst according to claim 1, wherein said active mass has the following composition:

$$Mo_{12}Fe_{0.4-4.0}Co_{0.4-4.0}Ni_{1.0-9.0}Bi_{0.2-2.0}P(As)_{0.2-2.0}K(Rb,Cs)_{0-0.1}Sm_{0.01-0.2}Si_{5-40}O_x,$$

wherein the element silicon is present as pyrogenic or highly-dispersed precipitated silicic acid, silicic acid brine or fine-particle aluminum silicate and wherein X denotes the number of oxygen atoms which satisfies the valences of the other elements.

7. A catalyst according to claim 6, wherein said element silicon is present as montmorillonite.

8. A catalyst according to claim 6, wherein said active mass has the following composition:

$$Mo_{12}Fe_{0.6-2.0}Co_{0.6-2.0}Ni_{2.0-6.0}Bi_{0.5-1.5}P(As)_{0.5-1.5}K(Rb,Cs)_{0.001-0.05}Sm_{0.02-0.1}Si_{10-30}O_x,$$

wherein the element silicon is present in the form of pyrogenic SiO$_2$ and montmorillonite in a weight ratio of 1:0.5 to 1:4 and wherein X denotes the number of oxygen atoms which satisfies the valences of the other elements.

9. A catalyst according to claims 6, 7, or 8 wherein said montmorillonite has a reduced specific BET surface area of less than 2.0 m$^2$/g.

10. A method for making the catalyst according to claim 1, comprising the following steps:

(a) mixing a suspension, obtained by combining salt solutions of said elements with the insoluble, silicon-containing carrier material, spray-drying the suspension thus obtained at an initial temperature of 300° C.-600° C., separating the resulting dry powder and heating at 120° C.-220° C. to thereby obtain a spray dried powder with an average particle diameter of less than 30 μm, wherein the time of heating the spray dried powder is between 2 and 25 seconds to thereby obtain a dry spray dried powder;

(b) calcining the dry spray dried powder in a kiln for 5 to 60 minutes whereby the temperature of the spray dried powder is raised to between 320° C. and 480° C.;

(c) extruding the calcined spray dried powder with 5 to 40 weight %, related to the weight of spray dried powder, of a pore forming agent which is completely decomposable at a temperature of less than 400° C., at a temperature of less than 80° C., in the desired geometrical shape, at a pressure of less than 50 bar, and subdividing the extruded strand by cutting it to the length of the desired body;

(d) drying the extruded individual bodies.

11. The process according to claim 10, wherein in step (c) there is also added a quantity of wetting agent, lubricant, and binding agent.

12. A method according to claim 11 wherein said lubricant is petroleum, water or a 1-10 weight % aqueous methylcellulose solution 13. A method according to claim 11 wherein said wetting agent and binding agent is a 1-10 weight % aqueous methylcellulose solution.

14. A method according to claims 12 or 13 in which said methylcellulose solution is in the form of an oil-in-water emulsion.

15. The process according to claim 10, further comprising after step (d) burning out the decomposable substance in said extruded individual bodies in a kiln and then tempering for 5 to 60 minutes at a temperature, measured in the pouring of the individual bodies, amounting to between 450° C. and 650° C. in an air current.

16. A method according to claim 10 wherein said pore forming agent is selected from the group consisting of pentaerythritol, cellulose powder, urea, oxalic acid, and polyvinyl alcohol.

17. A method according to claim 10 wherein said pore forming agent is solid pentaerythritol with an average particle diameter of less than 40 μm.

18. A method according to claim 10 wherein said binding agent is dry methycellulose powder.

19. A method according to claim 10 in which said burn-out and tempering of the extruded individual bodies occurs in separate steps.

20. A method according to claim 10, wherein said extruded individual bodies and air current during the burn-out process are conducted in a direct current.

21. A method according to claim 10, wherein said burn-out is performed at a maximum of 400° C.

* * * * *